(12) United States Patent
Münzenberg et al.

(10) Patent No.: US 6,274,755 B1
(45) Date of Patent: Aug. 14, 2001

(54) PROCESS FOR THE PRODUCTION OF POLYSULFIDE SILANE COMPOUNDS

(75) Inventors: Jörg Münzenberg, Hanau; Rudolf Michel, Freigericht, both of (DE)

(73) Assignee: Degussa-Huls AG, Frankfurt am Main (DE)

( * ) Notice: Subject to any disclaimer, the term of this patent is extended or adjusted under 35 U.S.C. 154(b) by 0 days.

(21) Appl. No.: 09/607,953

(22) Filed: Jun. 30, 2000

(30) Foreign Application Priority Data

Jul. 1, 1999 (DE) .............................. 199 30 495

(51) Int. Cl.$^7$ ....................................... C07F 7/08
(52) U.S. Cl. .............................................. 556/427
(58) Field of Search ............................... 556/427

(56) References Cited

U.S. PATENT DOCUMENTS 5,663,396 * 9/1997 Musleve et al. .................... 556/427
6,140,524 * 10/2000 Ichinohe et al. .................... 556/427
6,194,595 * 2/2001 Michel et al. ....................... 556/427

\* cited by examiner

*Primary Examiner*—Paul F. Shaver
(74) *Attorney, Agent, or Firm*—Pillsbury Winthrop LLP

(57) ABSTRACT

Process for the production of polysulfide silane compounds of the general formula $$Z\text{-}R^1\text{-}S_n\text{-}R^1\text{-}Z \qquad (I)$$

wherein silylalkyl halides of the formula $$ZR^1X \qquad (II)$$

are reacted with alkali metal polysulfides of the formula $$M_2S_n, \qquad (III)$$

wherein
alkali metal polysulfides $M_2S_n$ are obtained by reacting alkali metal hydroxides of the general formula (IV)

$$MOH \qquad (IV)$$

and elemental sulfur in a non-aqueous solvent or without solvent.

1 Claim, No Drawings

PROCESS FOR THE PRODUCTION OF POLYSULFIDE SILANE COMPOUNDS

CROSS-REFERENCE TO RELATED APPLICATION

This application is based on German Application DE 199 30 495.5, filed Jul. 1, 1999, which disclosure is incorporated herein by reference.

FIELD OF THE INVENTION

This invention relates to a process for the production of polysulfide silane compounds.

BACKGROUND OF THE INVENTION

Silica-filled rubber articles are known in the rubber industry. In comparison with prior technology, these rubber articles have various advantages, such as, for example, in the tire sector, inter alia, improved wet skid behavior and lower rolling resistance are provided. Polysulfide silane compounds are used as additives in order to achieve such good characteristics. These compounds act as coupling agents between the filler, silica and the organic polymer and bring about a reduction in the viscosity of the composition during incorporation of the filler.

Various processes for the production of known polysulfide silanes are described in several patent applications. Most methods start from alkoxysilylalkyl halides which are reacted with alkali metal polysulfides produced in various manners.

According to U.S. Pat. No. 5,405,985, an alkali metal polysulfide is produced by reacting alkali metal sulfide with sulfur in an aqueous solution. The polysulfide coupling agents are obtained by reacting the resultant aqueous polysulfide solution with alkoxysilylalkyl halides in a phase-transfer catalyzed system. It is known that both alkoxysilylalkyl halides and the reaction products obtained therefrom are susceptible to hydrolysis. This process accordingly has the disadvantage that the polymers formed after hydrolysis and condensation exhibit no reinforcing action or exhibit a severely reduced reinforcing action when used in a rubber composition.

For this reason, anhydrous systems are used in other known processes. An anhydrous polysulfide may thus, for example, be obtained in an upstream synthesis step from elemental sulfur and elemental sodium (U.S. Pat. No. 4,640,832). Alternative production methods for anhydrous alkali metal polysulfides start from elemental sulfur and alcohols (U.S. Pat. No. 5,399,739) or from alkali metal alkoxides, hydrogen sulfide and sulfur (U.S. Pat. No. 5,596,116). Another variant uses alkali metal hydrogen sulfide and sodium alkoxide in combination with sulfur in order to produce the polysulfide (DE 3311340).

These known processes have the disadvantage that costly starting materials such as alkali metals or alkali metal alkoxides or the toxicologically and ecotoxicologically questionable compound hydrogen sulfide must be used in the production of sodium polysulfide.

It is furthermore known to dry commercially available "anhydrous" sodium sulfide and then to react it with sulfur in organic solvents. The hydrous sodium sulfide is dried both by contact drying under reduced pressure (JP 7228588, DE 19755760, EP 361998) and by azeotropic drying methods (DE 19610281, JP 7228588). These known processes have the disadvantage that sodium sulfide has a strong tendency to melt on heating which means that even slight deviation from optimum conditions causes the material being dried to stick to the container walls with consequent losses of valuable product. Dried sodium sulfide moreover has a tendency to ignite spontaneously, such that elaborate safety precautions are required for drying, which make the process uneconomic for industrial application.

U.S. Pat. No. 5,663,396 discloses a process in which the polysulfide is produced in an aqueous solution from sodium hydroxide solution and sulfur. The resultant polysulfide solution is then in turn reacted with alkoxysilylalkyl halides in a phase-transfer catalyzed system. There is a great risk in this procedure too that some of the starting compound or product will be reacted to yield polymers which are ineffective for practical application.

In view of the above-described disadvantages of the prior art, there was a requirement for a process which is straightforward to perform industrially and is simultaneously economically viable for the production of anhydrous alkali metal polysulfides, which may be used for the production of the stated polysulfide silane compounds.

SUMMARY OF THE INVENTION

The present invention provides a process for the production of polysulfide silane compounds of the general formula (I)

$$Z-R^1-S_n-R^1-Z, \qquad (I)$$

in which $R^1$ represents branched or unbranched alkyl groups having 1 to 8 C atoms and optionally interrupted by O, N or S atoms or alkylaromatics of the type $(CH_2)_p Ph (CH_2)_p$ having 8 to 14 C atoms, wherein p is an integer from 1 to 4 and n is an integer from 1 to 4, Z represents residues of the type $(R^2O)_{3-m}R^2_m Si$, in which the residues $R^2$ may be identical or different and are branched or unbranched alkyl residues having 1 to 6 C atoms, and m is 0, 1 or 2, wherein silylalkyl halides of the general formula (II)

$$ZR^1X, \qquad (II)$$

in which X corresponds to Cl, Br or I and Z and $R^1$ have the above-stated meanings, are reacted with alkali metal polysulfides of the general formula (III)

$$M_2S_n, \qquad (III)$$

wherein

M denotes the alkali metals Na and K and n has the above-stated meaning, which process is characterized in that the alkali metal polysulfides $M_2S_n$ are obtained by reacting alkali metal hydroxides of the general formula (IV)

$$MOH, \qquad (IV)$$

in which M has the above-stated meaning, with elemental sulfur in a non-aqueous solvent or without solvent.

The alkali metal polysulfide may be produced under protective gas at standard pressure or under reduced pressure, wherein the resultant water is distilled off. Nitrogen, helium or argon may be used as the protective gas. The pressure range may be from 1 bar to 0.1 mbar. The reaction temperature may be from 50° C. to 250° C., preferably from 80° C. to 150° C. Once the exothermic reaction has subsided, the reaction may be taken to completion by maintaining a temperature of 100° C. to 250° C., preferably 130° C. to 170° C., for a period of 0.5 to 4 hours, preferably 2 to 3 hours.

Non-aqueous solvents which may be used are high-boiling ethers or polyethers, saturated hydrocarbons or aromatics, preferably xylene, mesitylene or naphthalene, or mixtures thereof.

The process according to the invention has the advantage over the prior art that it may be performed in a virtually anhydrous system. Any water arising during the reaction between the alkali metal hydroxide and sulfur is removed from the product during the reaction, such that the alkali metal polysulfide, which is obtained as a solid, may be reacted in an anhydrous system to yield alkoxysilylalkyl polysulfides.

DETAILED DESCRIPTION OF THE PREFERRED EMBODIMENTS

EXAMPLE 1

60.0 g of fine NaOH pellets and 43.3 g of sulfur powder are initially introduced into a 500 ml three-necked flask equipped with a water separator and internal thermometer and containing 200 ml of xylene. The mixture is heated to 110° C. under nitrogen. A weakly exothermic reaction is observed at this temperature. The temperature is then raised to 130° C. wherein the water formed (approx. 12 ml) is removed by azeotropic distillation. After cooling, xylene is decanted off from the resultant yellow solid. The yellow solid is resuspended in 160 ml of ethanol under dry nitrogen and combined with 163.0 g of 3-chloropropyltriethoxysilane. The temperature is then raised to 60° C. At this temperature, an exothermic reaction is again observed, which heats the reaction mixture to boiling temperature. After the exothermic reaction has subsided, the mixture is refluxed for a further 2 h, cooled and the resultant solid removed by filtration. The filter cake is washed three times with 100 ml portions of ethanol. The collected filtrates are evaporated in a rotary evaporator at 110° C. under a readjusted vacuum. 149.1 g of a yellow liquid are obtained (yield: 93% relative to introduced 3-chloropropyltriethoxysilane). According to the $^1$H NMR spectrum, the product consists of a polysulfane mixture having an average sulfur chain length of 2.1.

EXAMPLE 2

60.0 g of fine NaOH pellets and 40.0 g of pulverulent sulfur are initially introduced into a 500 ml flask provided with grooves longitudinally. After the contents of the flask had been homogenized, the flask was connected to a rotary evaporator and evacuated to 1 mbar. The temperature is then raised to 100° C. in an oil bath while the flask is slowly rotated. At this temperature, a color change of the flask contents from yellow to orange is observed. At an oil bath temperature of 110° C., a strongly exothermic reaction develops and water is liberated. After this exothermic reaction has subsided, the temperature is raised to 170° C. and maintained at this level for 3 h to homogenize the reaction mixture and complete the reaction. After cooling to room temperature and flushing with dry nitrogen, 86.9 g of an orange/yellow solid are isolated.

78.2 g of this solid are initially introduced into a 500 ml three-necked flask equipped with a reflux condenser and internal thermometer under dry nitrogen in 195 ml of ethanol and heated to 55° C. together with 195.1 g of 3-chloropropyltriethoxysilane. An exothermic reaction is observed at this temperature, which heats the reaction mixture to boiling temperature. After this exothermic reaction has subsided, the reaction is continued for a further 2 h with refluxing and the temperature is then reduced to room temperature. The resultant solid is removed by filtration and the filter cake washed three times with 100 ml portions of ethanol. The combined filtrates are evaporated in a rotary evaporator at 110° C. under a readjusted vacuum. 179.4 g of a yellow liquid are obtained (yield: 93% relative to introduced 3-chloropropyltriethoxysilane). According to the $^1$H NMR spectrum, the product consists of a polysulfane mixture having an average sulfur chain length of 2.1.

EXAMPLE 3

60.0 g of fine NaOH pellets and 72.1 g of pulverulent sulfur are initially introduced into the flask of Example 2. After the contents of the flask had been homogenized, the flask was connected to a rotary evaporator and evacuated to 1 mbar. The temperature is then raised to 100° C. in an oil bath while the flask is slowly rotated At this temperature, a deepening of the color is observed. At an oil bath temperature of 110° C., a strongly exothermic reaction develops and water is liberated. After this exothermic reaction has subsided, the temperature is raised to 170° C. and maintained at this level for 3 h to homogenize the reaction mixture and complete the reaction. After cooling to room temperature and flushing with dry nitrogen, 115.6 g of an orange/yellow solid are isolated.

59.3 g of this solid are initially introduced into a 500 ml three-necked flask equipped with a reflux condenser and internal thermometer under dry nitrogen in 150 ml of ethanol and heated to 55° C. together with 114.4 g of 3-chloropropyltriethoxysilane. An exothermic reaction is observed at this temperature, which heats the reaction mixture to boiling temperature. Once this exothermic reaction has subsided, the reaction is continued for a further 2 h with refluxing and the temperature is then reduced to room temperature. After addition of a filter aid, the resultant solid is removed by filtration and the filter cake washed three times with 50 ml portions of ethanol. The combined filtrates are evaporated in a rotary evaporator at 110° C. under a readjusted vacuum. 119.7 g of a yellow liquid are obtained (yield: 94% relative to introduced 3-chloropropyltriethoxysilane). According to the $^1$H NMR spectrum, the product consists of a polysulfane mixture having an average sulfur chain length of 3.7.

EXAMPLE 4

15 84.2 g of KOH powder and 40.1 g of pulverulent sulfur are initially introduced into the flask of Example 2. After the contents of the flask had been homogenized, the flask was connected to a rotary evaporator and evacuated to 1 mbar. The temperature is then raised to 80° C. in an oil bath while the flask is slowly rotated. At this temperature, a color change to yellow/orange is observed. A strongly exothermic reaction develops and water is also liberated. After this exothermic reaction has subsided, the temperature is raised to 160° C. and maintained at this level for 3 h to homogenize the reaction mixture and complete the reaction. After cooling to room temperature and flushing with dry nitrogen, 102.0 g of an orange/yellow solid are isolated.

55.4 g of this solid are initially introduced into a 500 ml three-necked flask equipped with a reflux condenser and internal thermometer under dry nitrogen in 200 ml of ethanol and heated to 55° C. together with 114.4 g of 3-chloropropyltriethoxysilane. An exothermic reaction is observed at this temperature, which heats the reaction mixture to boiling temperature. After this exothermic reaction has subsided, the reaction is continued for a further 2 h with refluxing and the temperature is then reduced to room temperature. The resultant solid is removed by filtration and the filter cake washed twice with 50 ml portions of ethanol. The combined filtrates are evaporated in a rotary evaporator at 110° C. under a readjusted vacuum. 102.4 g of a brown liquid are obtained (yield: 91% relative to introduced 3-chloropropyltriethoxysilane). According to the $^1$H NMR spectrum, the product consists of a polysulfane mixture having an average sulfur chain length of 2.0.

What is claimed is:

1. A process for the production of polysulfide silane compounds of the general formula (I)

$$Z\text{-}R^1\text{-}S_n\text{-}R^1\text{-}Z, \tag{I}$$

in which
  $R^1$ represents branched or unbranched alkyl groups having 1 to 8 C atoms and while may be interrupted by O, N or S atoms or alkylaromatics of the type $(CH_2)_p Ph (CH_2)_p$ having 8 to 14 C atoms, wherein p is an integer from 1 to 4 and n is an integer from 1 to 4, and
  Z represents residues of the type $(R^2O)_{3-m}R^2_m Si$, in which the residues $R^2$ may be identical or different and consist of branched or unbranched alkyl residues having 1 to 6 C atoms and m is 0, 1 or 2, comprising:
    reacting silylalkyl halides of the general formula (II)

$$ZR^1X, \tag{II}$$

in which X corresponds to Cl, Br or I and Z and $R^1$ have the above-stated meanings, with alkali metal polysulfides of the general formula (III)

$$M_2S_n, \tag{III}$$

wherein
  M denotes the alkali metals Na and K and n has the above-stated meaning,
  wherein the alkali metal polysulfides $M_2S_n$ are obtained by:
    reacting alkali metal hydroxides of the general formula (IV)

$$MOH, \tag{IV}$$

in which M has the above-stated meaning, with elemental sulfur, in a non-aqueous solvent or without solvent.

* * * * *